United States Patent [19]
Poler

[11] Patent Number: 5,370,687
[45] Date of Patent: Dec. 6, 1994

[54] IMPLANTABLE DEVICE AND METHOD FOR IMPEDING SECONDARY GROWTH WITHIN AN EYE

[76] Inventor: Stanley Poler, 78 E. Second St., New York, N.Y. 10003

[21] Appl. No.: 984,217

[22] Filed: Nov. 30, 1992

Related U.S. Application Data

[63] Continuation of Ser. No. 791,992, Nov. 14, 1991, abandoned.

[51] Int. Cl.$^5$ .............................................. A61F 2/16
[52] U.S. Cl. .................................................. 623/6
[58] Field of Search ........................................ 623/6

[56] References Cited

U.S. PATENT DOCUMENTS 4,085,467  4/1978  Rainin et al. .......................... 623/6

*Primary Examiner*—Randy C. Shay
*Attorney, Agent, or Firm*—Hopgood, Calimafde, Kalil & Judlowe

[57] ABSTRACT

Epithelial-cell and protein-strand development, following eye surgery such as an intracapsulary lens extraction and intraocular-lens implantation, is retarded or impeded by providing small amounts of metal and/or basic salt in the environment or in the construction of an intraocular lens. It is believed that the use of one or more metals or a basic salt will provide an electrolytic action within the capsule and that cell growth and motility are thereby materially reduced. The electrolytic action is accompanied by an associated change in the oxygen availability that would otherwise have aided cell regrowth. Stated in other words, the changed Ph, temperature and chemical balance that result from a metal or basic-salt presence within the capsule reduces or eliminates the ability of epithelial cells to multiply.

40 Claims, 6 Drawing Sheets

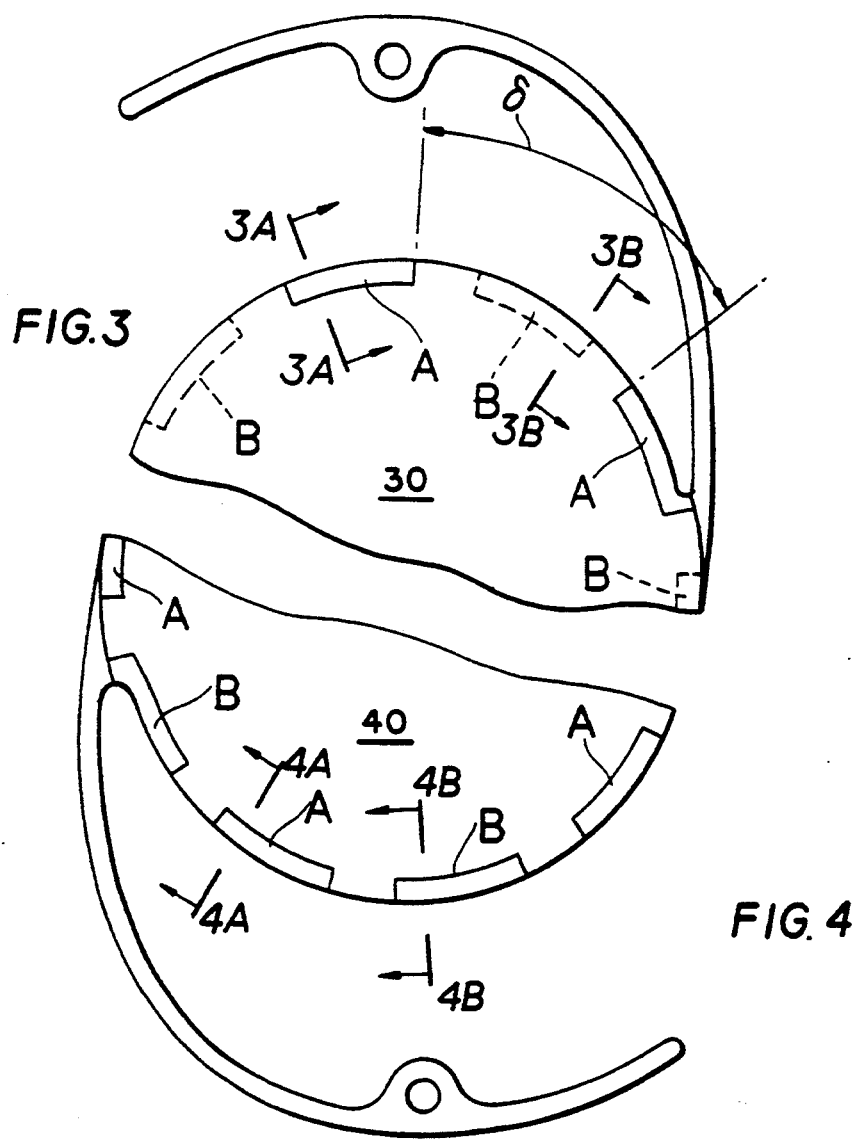
FIG. 3
FIG. 4
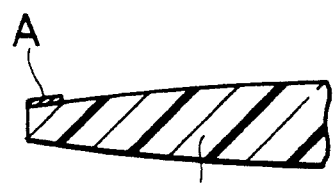
FIG. 3A
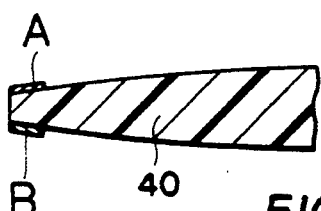
FIG. 4A
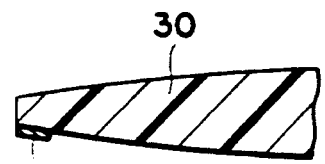
FIG. 3B
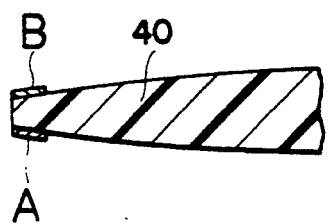
FIG. 4B

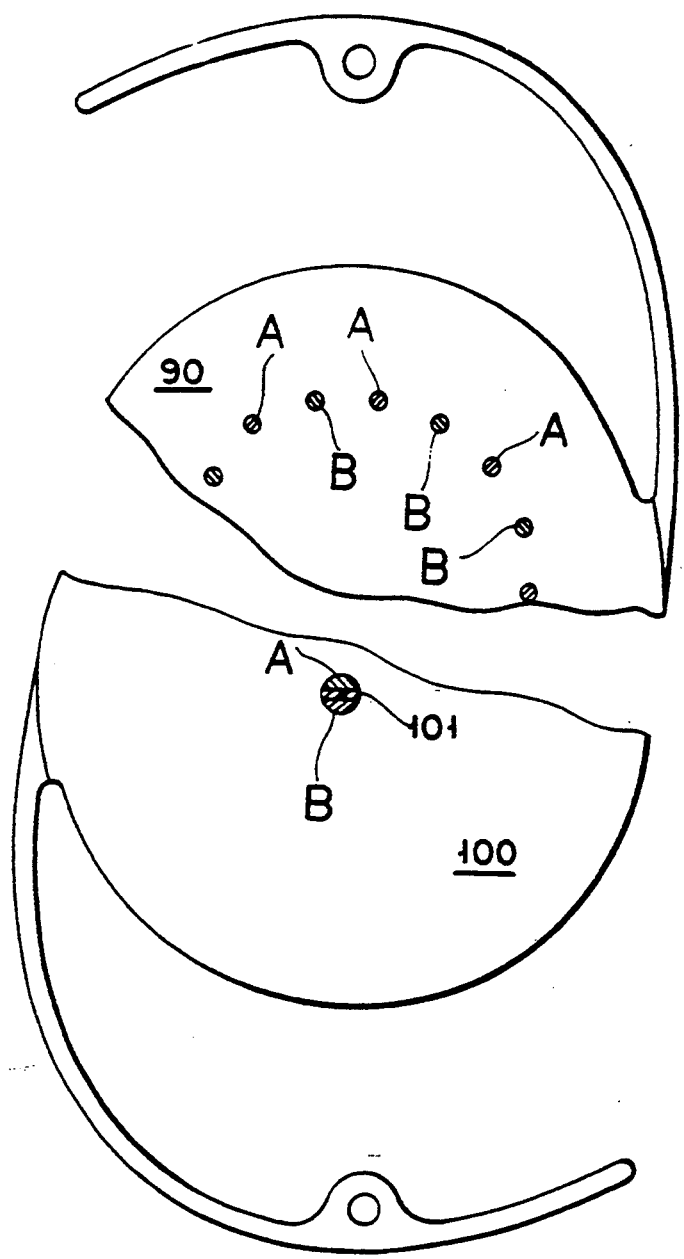
FIG. 9
FIG. 10
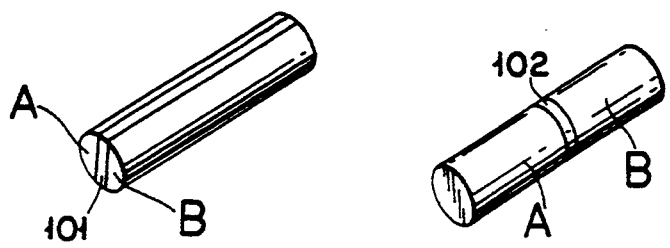
FIG. 10A          FIG. 10B

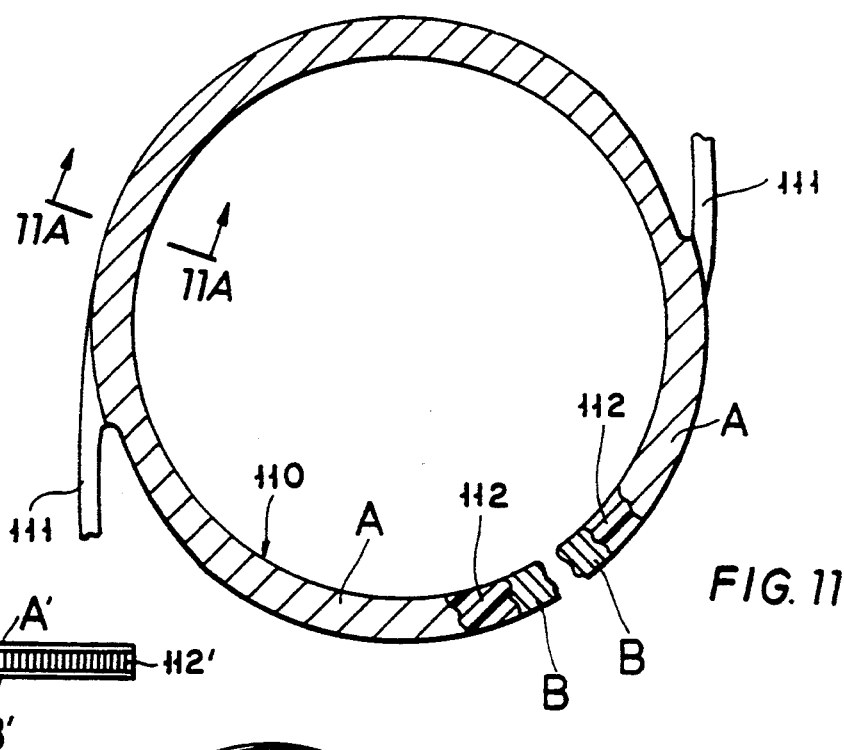
FIG. 11
FIG. 11A
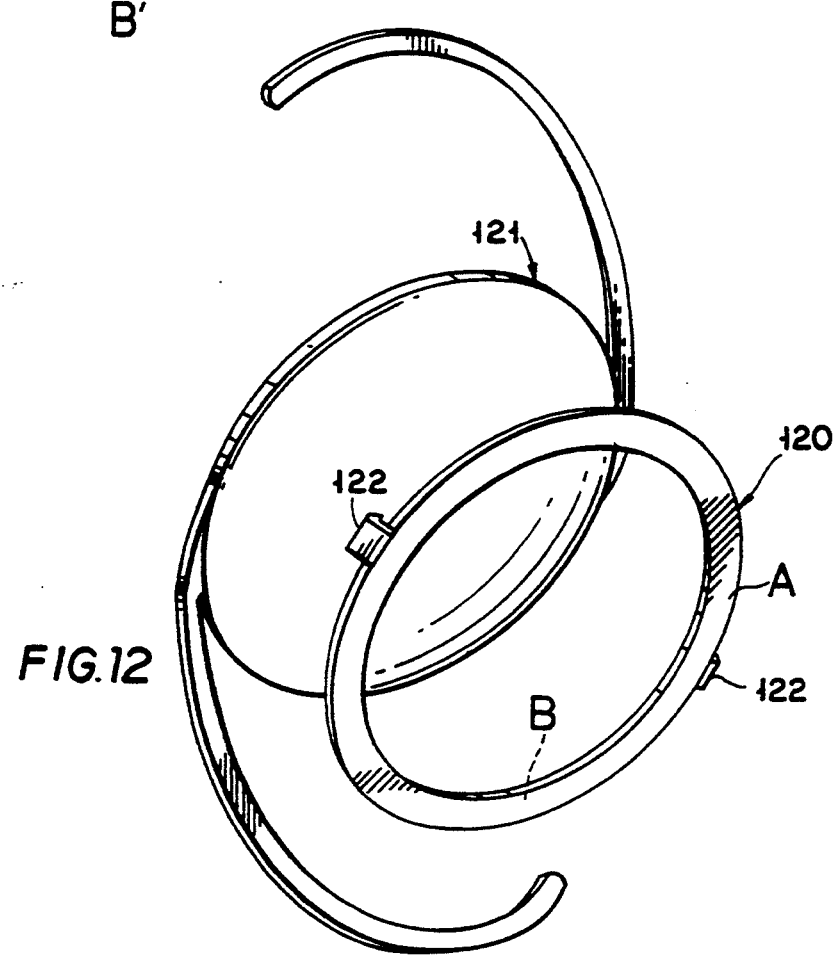
FIG. 12

IMPLANTABLE DEVICE AND METHOD FOR IMPEDING SECONDARY GROWTH WITHIN AN EYE

This is a continuation of copending application Ser. No. 07/791,992, filed Nov. 14, 1991 now abandoned.

BACKGROUND OF THE INVENTION

The invention relates broadly to eye-implantable means for impeding secondary growth within an eye; more particularly, the invention also relates to such means for impeding or preventing cell growth over one or more optically used surfaces after an intraocular-lens has been implanted, as in the case of a posterior-chamber lens mounted in the lens capsule of an eye, following extracapsular cataract extraction.

In the United States, the use of lens implants in replacement of cataract extractions has been a growing practice since 1975, to the point that this year the vast majority of the million or so patients having a cataract extraction will receive an intraocular-lens implant. Such implants have almost totally replaced the use of thick eyeglasses or contact lenses as a means of correcting refraction and restoring close-to-normal vision.

Over this 16-year period, the techniques of removing a cataract have undergone great change. A large majority of the diseased tissue was removed using a technique known as "intra-capsular extraction". This technique requires making a relatively large incision in the eye, and removing the lens of the eye entirely. Intraocular lenses are then inserted to be supported by the iris, or in the anterior chamber.

This technique has its limitations, so that equipment and techniques have been developed that allow the lens capsule to be cut, a probe inserted, and energy applied to fragment the nuclear lens material. Through a technique of ultrasonic or pulsed laser delivery (phacoemulsification), in conjunction with irrigation and aspiration, fragmented lens-cortical material is removed from the eye.

There are two methods of placing an artificial lens. Some physicians choose to place a lens anteriorly to the lens capsule. Others choose to insert it within the human capsule, a technique known as capsular fixation. The majority of lens implants today use the capsular-fixation technique.

After extra-capsular extraction, and intraocular-lens implantation, a large number of these lenses become opaque, by reason of epithelial-cell growth and protein-strand development over one or more optically used surfaces. In some cases this occurs immediately, and in other cases, it occurs many months after surgery. Ophthalmologists have developed techniques of scraping and cleaning the human-lens capsule in order to remove human-lens epithelial cells and thereby reduce the amount of opacification. However, because of the size and relative concentration of these cells at the capsular perimeter or equatorial zone, such techniques have not been completely successful, in that those cells which remain after a scraping or cleaning procedure are available to replicate and spread, and thus to form an opacifying epithelium layer of protein strands, over the optically used surface of the implanted lens. As a result, post-operative secondary procedures are required to clear the lens, and it is evident that these intra-operative techniques cannot be considered to be successful.

In addition to intra-operative cleaning procedures to remove these capsule cells, two alternative post-operative techniques are in use today, to clear the epithelial cells and protein strands from an opacified lens. The more common technique uses a YAG laser to direct a high-energy burst at the opacifying membrane. After repeated bursts, the membrane is ripped and a large enough area is cleared to return vision to the patient. The procedure may have to be repeated frequently on certain patients.

The alternative procedure involves manipulated insertion of a small needle or other instrument into the eye, under a local or general anesthesia. The physician observes the membrane and pulls the membrane away from the optic.

Both of these alternative procedures entail significant risks to the patient, not to mention the cost and inconvenience to the patient. Additionally to the re-growth of epithelium and protein strands, some implanted lenses opacify because they accumulate pigment or other deposits which reduce the optical properties of the lens.

Dr. Hoffer and his U.S. Pat. No. Re. 31,626 are illustrative of the fact that ophthalmologists have long recognized the opacification problem with intraocular-lens implants. His particular contribution to solving the problem was to form a sharp annular ridge or "dam" feature into the posterior surface of an intraocular lens, and this dam establishes peripheral contact with the posterior capsule, to prevent proliferating-cell advance from the equatorial zone to the optically used region of the posterior surface of the lens. Even so, Dr. Hoffer recognized that cell re-growth could ultimately be the cause of further opacification of the lens, because he provided an access space in the otherwise circumferential continuity of his ridge, so that a surgeon could manipulate a knife through the access space, to remove an opacifying accumulation from the posterior optical surface of the implanted lens. But the extent of professional debate on the Hoffer approach casts doubt on efficacy of the technique.

BRIEF STATEMENT OF THE INVENTION

It is an object of the invention to provide eye-implantable means for impeding secondary growth within an eye, particularly following surgery such as an extra-capsulary extraction wherein normal growth equilibria have been surgically disturbed.

It is also an object of the invention to provide an improved structure for use in or in connection with an intraocular lens, wherein said structure has the inherent capability of eliminating or greatly reducing epithelial-cell growth and protein formation on the lens itself.

Another object is to meet the above object while, at the same time, reducing the adherence to the lens surface of pigmentation and other deposits.

Still another object is to provide an eye-implantable structure which can change the surface energy and thereby change the wetting angle of an intraocular lens, to thereby reduce the adherence of deposits.

A further object is to meet the foregoing objects by providing an intraocular-lens construction which will so directly or indirectly react with capsular epithelial cells as to significantly inhibit or reduce their rate of replication following an extracapsulary extraction.

Still another object is to provide an improved intraocular lens with a coating which will produce both therapeutically beneficial action in an eye-implanted environment, as well as improved optical qualities.

The invention achieves these objects by providing small amounts of metal and/or basic salt in the environment or in the construction of an intraocular lens. It is believed that the use of one or more metals or a basic salt will provide an electrolytic action within the capsule and that cell growth and motility are thereby materially reduced. The electrolytic action is accompanied by an associated change in the oxygen availability that would otherwise have aided cell regrowth. Stated in other words, the changed Ph, temperature and chemical balance that result from a metal or basic-salt presence within the capsule reduces or eliminates the ability of epithelial cells to multiply.

DETAILED DESCRIPTION

The invention will be described in detail for various specific embodiments and methods, in conjunction with the accompanying drawings, in which:

FIG. 1. is a plan view of an intraocular lens of the invention;

FIG. 3 is a plan view, fragmented to show approximately one half of another intraocular lens of the invention;

FIG. 3A is a sectional view taken at the plane 3A—3A of FIG. 3;

FIG. 3B is a sectional view taken at the plane 3B—3B of FIG. 3;

FIG. 4 is a plan view, fragmented as in FIG. 3, to show another intraocular lens of the invention;

FIG. 4A is a sectional view taken at the plane 4A—4A of FIG. 4;

FIG. 4B is a sectional view taken at the plane 4B—4B of FIG. 4;

FIG. 9 is a plan view, fragmented as in FIG. 3, to show another intraocular lens of the invention;

FIG. 10 is a plan view, fragmented so as to include the central region of still another intraocular lens of the invention;

FIG. 10A is a view in perspective, to show a component central part of the lens of FIG. 10;

FIG. 10B is a view similar to FIG. 10A, to show a modification;

FIG. 11 is a fragmentary plan view, partly broken-away to show construction, of a first lens-less embodiment of the invention;

FIG. 11A is an enlarged sectional view, taken at 11A—11A of FIG. 11, to show a modification; and FIG. 12 is an exploded isometric view of a second lens-less embodiment of the invention, in relation to an intraocular lens to which it may be assembled.

Figure 1:
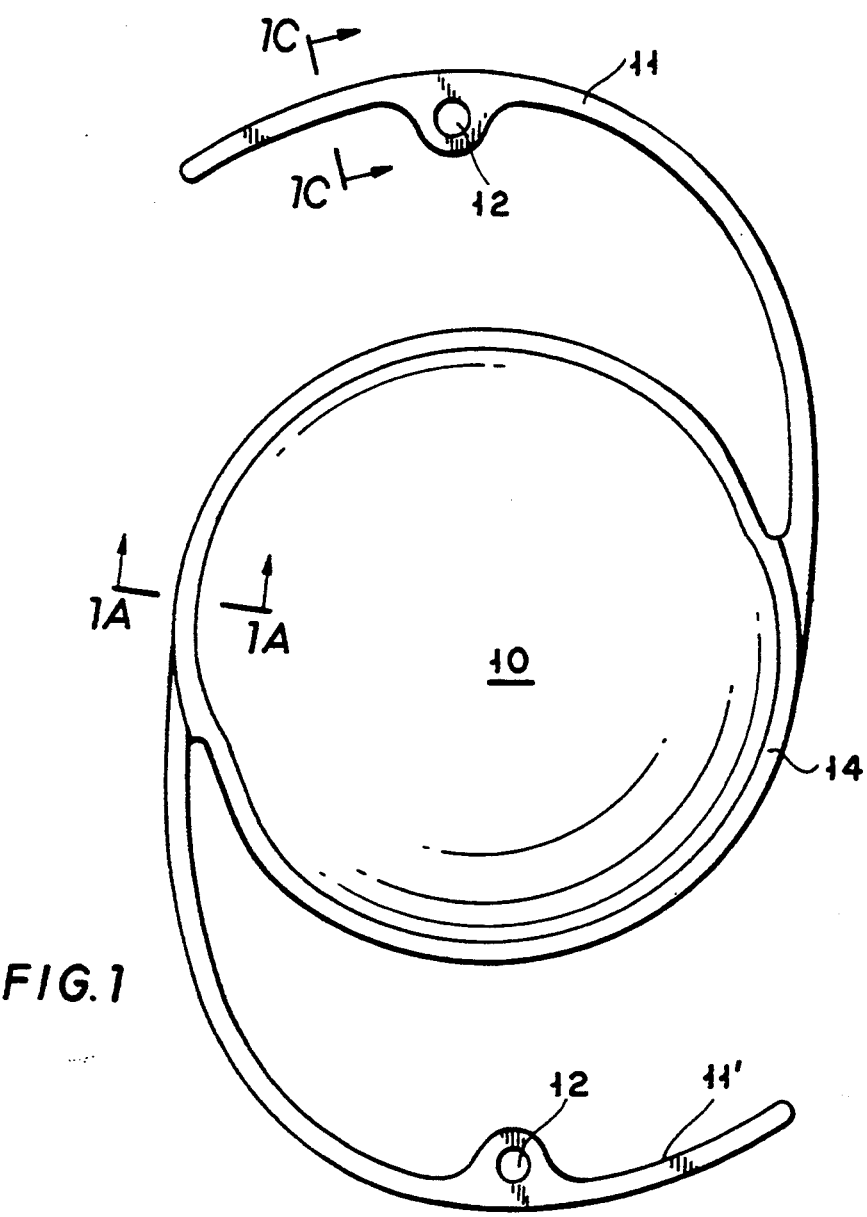
FIG. 1A is an enlarged fragmentary view in section, at the plane 1A—1A of FIG. 1.
FIG. 1B is a view similar to FIG. 1A, to show a first modification.
FIG. 1C is an enlarged sectional view at the plane 1C—1C of FIG. 1, to show a second modification.
Figure 1A:
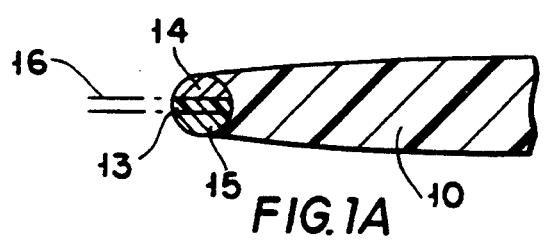

In the embodiment of FIGS. 1 and 1A, an intraocular lens assembly is seen to comprise a central generally circular lens element 10 which may be of glass, sapphire or other transparent material such as polymethylmethacrilate (PMMA) or silicone. Two gently compliant supporting haptic elements 11, 11' extend with diametric symmetry outwardly of lens element 10. An aperture 12 in each haptic aids in collapsing the assembly and otherwise in manipulation in a lens-implantation procedure. The haptic elements 11, 11' may be integral formations with lens element 10, but in the embodiment of the invention shown in FIGS. 1 and 1A, the haptics 11, 11' are integrally formed with a narrow annular ring 13, which serves as a flat insulating spacer between opposed rings 14, 15 of dissimilar metals. The dissimilar metals may be selected from the group comprising gold, rhodium, silver, copper, platinum and aluminum; thus ring 14 may be of gold and ring 15 may be of silver. The dissimilar metals should be benign to body fluids and be selected for a difference between their respective potentials, wherein the potential difference is in the range of 0.1 to 3.5 volts. In the case if a lens body wherein the dissimilar metals are exposed at opposite surfaces of the lens body, it is preferred that the one of these metals which has the greater potential in the electrochemical series shall be on or at the back surface of the lens body.

In FIG. 1A, the laminated assembly of metal rings 14, 15 to the opposite flat sides of annular ring 13 is seen to be of circular section, snap-fitted into a peripheral groove formation of lens element 10. Also, in FIG. 1A, phantom lines 16 will be understood to suggest outward formation of the haptics 11, 11', as having been integrally formed with ring 13. When implanted in an eye, the metal rings 14, 15 will both be exposed to conductive liquid within the eye, thus establishing a circumferentially continuous basis of electrolytic action within the eye; if installed within the capsule following a cataract extraction, the electrolytic action will be within the capsule, for reduction of the cell growth and motility which could otherwise be factors in an opacity development. More specifically, gold and silver were named at rings 14 and 15 in illustration of the facts (1) that these metals are benign to body cells and (2) that dissimilar metals and metal salts have different inherent potentials in the electrochemical series, so that in the saline environment within the eye, ion/electron flow is directional, from the silver (or silvered) rim or ring 15, around the rim of the lens assembly, and to the gold (or gilded) rim or ring 14.

Figure 1C:
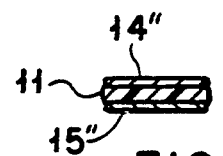
Figure 1B:
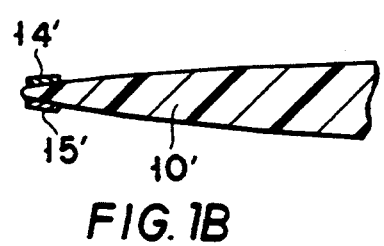

In the modification of Fig. 1B, the intraocular lens assembly of FIG. 1 may be viewed as an integral molded-plastic product, with haptics 11, 11' molded to lens element 10. And the peripheral rim designated 14 in FIG. 1 is seen as a metal layer 14' applied to the peripheral rim of one face of the lens element 10'; the peripheral rim of the opposite face of lens element 10' carries a similar layer 15' of a dissimilar metal. The layers 14', 15' may be plated to their respective faces of the lens element, or they may be formed by vacuum or other deposition or other known techniques, such as sputtering, and plasma-etching, but in any event they are permanently adhered components of the intraocular-lens assembly. Once implanted in the eye, electrolytic action is established as in the case of the embodiment of FIGS. 1 and 1A.

The modification of FIG. 1C serves to illustrate that, if desired, metal-plated regions 14", 15" of the opposed faces of one or both haptics may be sufficient to establish the electrolytic action, once implanted in an eye.

Figure 2:
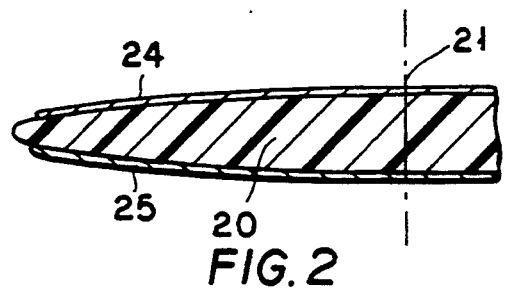
FIG. 2 is an enlarged fragmentary view in section, similar to FIG. 1B but showing a third modification.

In the embodiment of FIG. 2, the plan view of the assembled intraocular lens may again be as depicted in FIG. 1, except for the fact that optical coating in the form of a transparent first metal or basic-salt coating 24 characterizes one face of the lens element 20, while a transparent second and dissimilar metal or basic-salt coating 25 characterizes the opposite face of the same lens element. Schematic indication of the central axis 21 of lens element 20 will be understood to indicate that coatings 24, 25 cover the entire optically used central area of the lens, leaving an uncoated short circumferential rim portion of each face of the lens. The term "optical coating" as used herein will be understood to refer to visually transparent thin film coatings as are commercially available inter alia from The Optical Group of Perkin-Elmer Corporation, Wilton, Connecticut, in which case it is customary to specify coating thickness in terms of a specified fraction of a wavelength; it is Perkin-Elmer practice to assume an optical wavelength in the visible spectrum to be the HeNe line at 632.8-nm, for optical-coating thickness purposes, unless a customer identifies a different wavelength for specifying desired optical-coating thickness. In the present case, it is preferred that coating thickness shall be less than an optical wavelength, or that it shall be at least one half an optical wavelength.

The embodiments of FIGS. 3 and 4 are illustrative of different arrangements of angularly interlaced metal segments, wherein the dissimilar metals are denoted A and B, respectively. In the arrangement of FIG. 3, the near face of lens element 30 carries segmental peripheral platings of the first metal A (see FIG. 3A), and the opposite face of the same element 30 carries like segmental peripheral platings of the second (and dissimilar) metal B (see FIG. 3B). The spacing δ between adjacent platings A exceeds the angular width of a single such plating, and the spacing between adjacent platings B is also In the arrangement of FIG. 4, each face of lens δ. element 40 carries spaced segmental platings of metals A, B, in staggered angular interlace. In the sections taken for FIGS. 4A and 4B, it is seen that the segments on opposed faces are in register, but so staggered that platings A on one face register with platings B on the opposite face.

Figure 5:
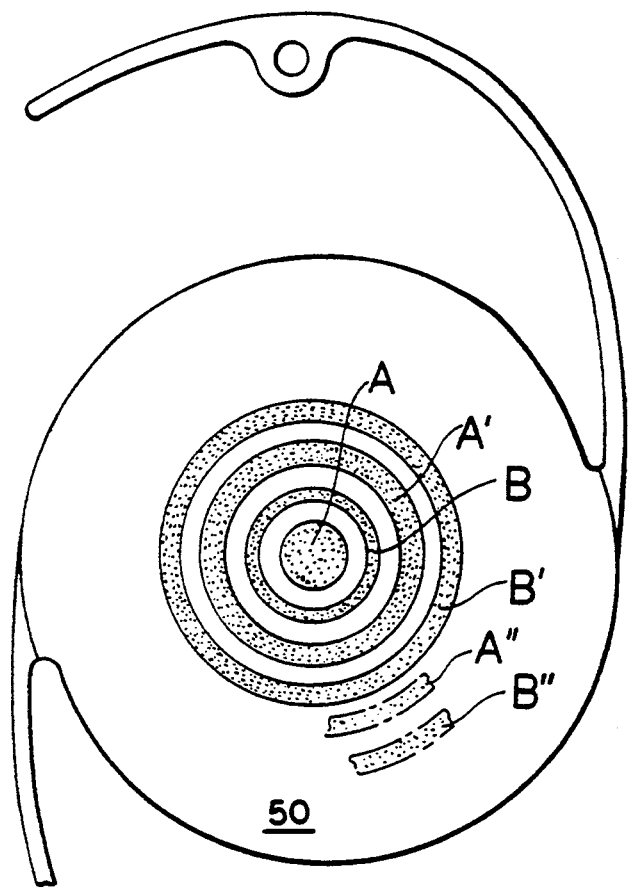
FIG. 5 is a plan view of another intraocular lens of the invention.

In the arrangement of FIG. 5, radially spaced transparent concentric annular coatings on one face of a lens element 50 are arrayed such that coatings A, A', A" of the first metal are in radially staggered interlace with coatings B, B', B" of the dissimilar second metal.

Figure 6:
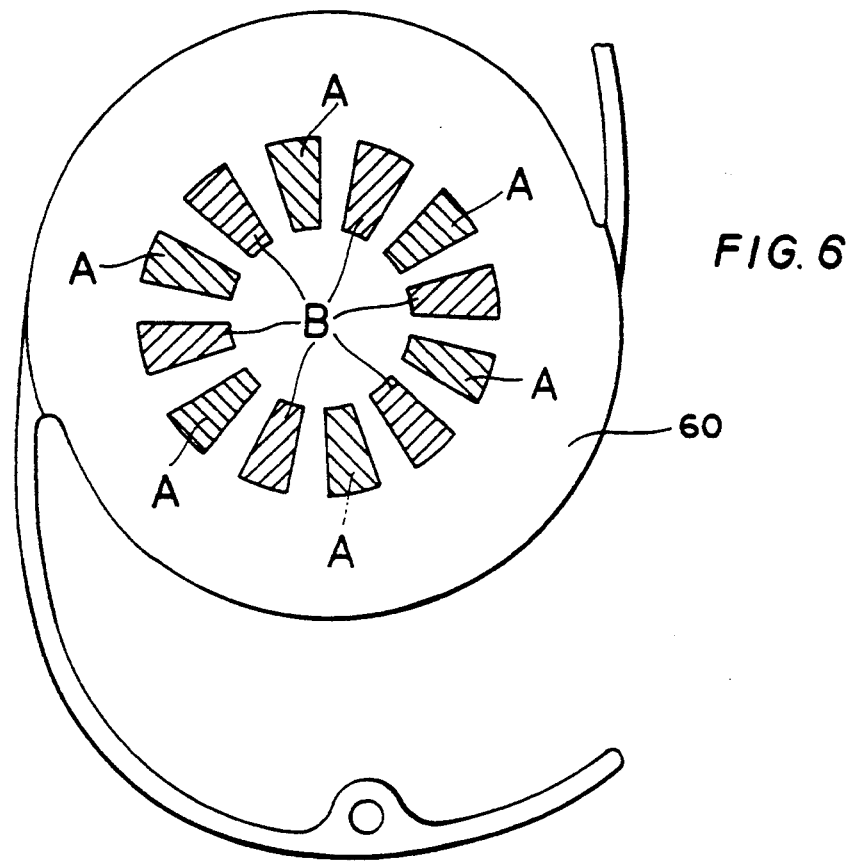
FIG. 6 is a plan view of another intraocular lens of the invention.

The arrangement of FIG. 6 involves an angularly spaced succession of sector-shaped coatings on a single face of lens element 60, wherein coatings of the first metal A ( with direction of cross-hatching) are in angularly staggered with coatings of the second and dissimilar metal B (shown with the opposite direction of cross-hatching).

Figure 7:
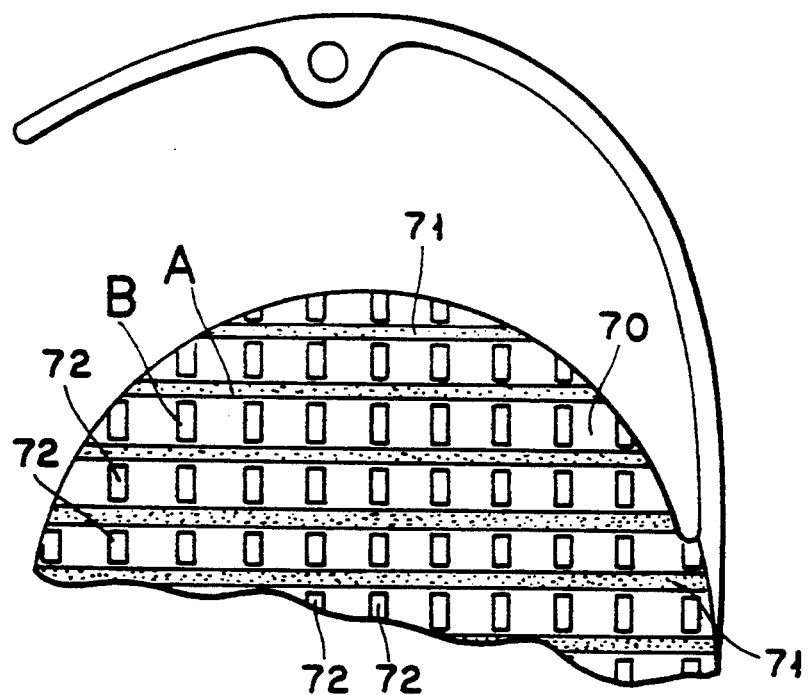
FIG. 7 is a plan view, fragmented as in FIG. 3, to show another intraocular lens of the invention.

In the arrangement of FIG. 7, a single face of a lens element 70 is arrayed with grid-like transparent coatings, wherein spaced parallel strips 71 of a first coating of metal A, are so spaced as to accommodate (between strips 71) spaced segments 72 of a second coating, of metal B, the segments 72 being elongate in the direction transverse to the direction of strips 71 and being preferably in aligned transverse rows, as shown, and avoiding any physical contact between the two metals A, B.

Figure 8:
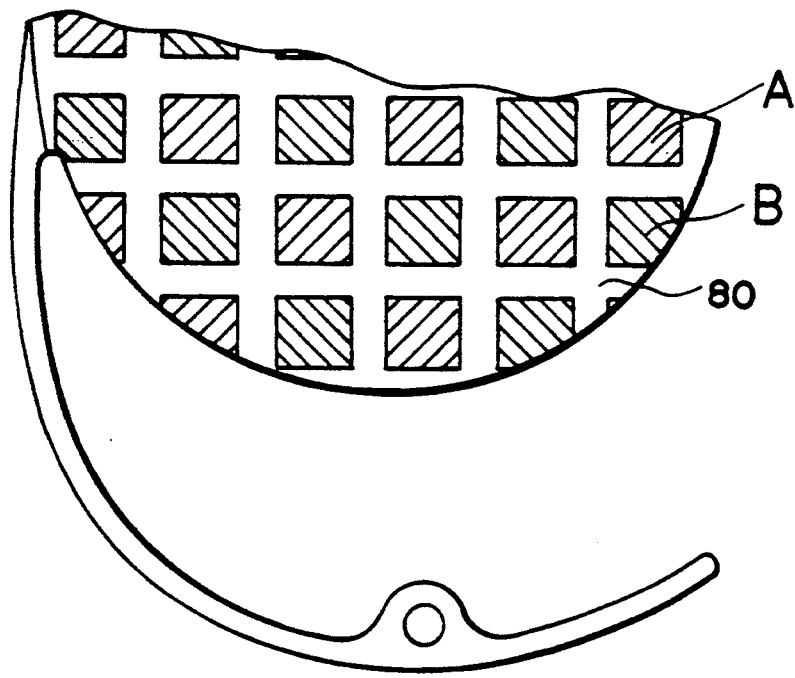
FIG. 8 is a plan view, fragmented as in FIG. 3, to show another intraocular lens of the invention.

In the arrangement of FIG. 8, a single face of lens element 80 is coated with a grid pattern of geometric squares which are spaced from each other in each of two dimensional directions, and which are in a two-dimensionally interlaced pattern of alternating dissimilar metals A, B. As in FIG. 6, one direction of cross-hatching will be understood to denote metal-A coatings, and the opposite direction of cross-hatching will be understood to denote metal-B coatings.

FIGS. 9 and 10 represent departures from previously described embodiments, in that the involved dissimilar metals (A, B) incorporated in the intraocular-lens assembly are in the form of metal pins or studs, which can be readily pressed or molded into final position, e.g., as part of the molding process for forming the lens element and its haptics. In the arrangement of FIG. 9, these pins or studs are in angularly spaced array, of metal A being in alternation and thus in interlace relation with pins of metal B, on a circular locus of the array about and at radial offset from the center of the lens element 90. The ends of these pins may be flush with one or with each of the opposed surfaces of the lens element 90.

In the arrangement of FIG. 10, a single central pin is incorporated in a lens element 100, as in the course of molding the lens element; alternatively, the central pin may be pressed into assembled relation with the lens element. This single central pin is seen in FIGS. 10 and 10A to be overall cylindrical, with an elongate spacer or shim 101 of insulating material in essentially a diametral plane of spacing a chord-truncated half cylinder of metal A from a chord-truncated half cylinder of metal B. The length of the consolidated cylinder of FIGS. 10 and 10A may be short of the full axial thickness of lens element 100, with exposure of both metals at one to the exclusion of the other face of the lens element; alternatively, the length of this cylinder may match the full axial thickness of lens element 100 for exposure of both metals at the center of each face of the lens element.

FIG. 10B illustrates a modification of the central-pin concept of FIGS. 10 and 10A, in that the cylindrical pin of FIG. 10B is a longitudinal consolidation of short cylinders of the dissimilar metals A, B, with an insulating circular spacer 102 therebetween. If the two short cylinders of metals A and B, respectively, are initially supported at opposite sides of the mold cavity for the lens element 100, then the molding of lens element will automatically establish spacer 102 as an integral part of the finished lens, with the axially outer end of each small cylinder exposed at a different one of the opposite faces of the lens element.

In the discussion thus far, all uses of dissimilar metals or salts have been as integral components of an intraocular lens. But the invention need not be thus limited. For example, FIG. 11 illustrates that an independent implantable structure having no lens component may be the means of providing the desired electrolytic environment within an eye, thus providing a means of treating uveitis, quite aside from intraocular-lens considerations. In FIG. 11, an open ring 110 having a molded plastic body 112 with integral haptic formations 111 may be coated with first metal A on one of its annular faces and with the second and dissimilar metal B on its opposite annular face. In FIG. 11, ring 110 is partly broken-away, to permit separate identification of the metal coating A on one side of the plastic body 112, and of the other metal coating B on the opposite side of body 112, with opposite directions of cross-hatching to denote the respective metal coatings. And of course, the diameter of the central opening of ring 110 exceeds the optically used central area of the lens, whether it be the natural lens or an intraocular lens.

Lacking a lens component, the device of FIG. 11 may be extremely light and flexible, permitting its readily manipulable implantation adjacent and anterior to an installed intraocular lens. Alternatively, if installed prior to intraocular-lens implantation, the device of FIG. 11 will be adjacent but posterior to the implanted lens, where the electrolytic environment it generates may be deemed more appropriate for retarding the natural tendency for opacifying growth over the posterior surface of the lens.

The enlarged sectional view of FIG. 11A is illustrative of a modification wherein the outer layers of dissimilar metal coatings A', B' are porous and wherein the ring body 112' to which they are applied is foraminated or otherwise porous between its A-B coated surfaces. The foraminations are shown schematically as a multiplicity of through-passages which become wetted with saline fluid within the eye and therefore afford a corresponding multiplicity of paths and enhanced area for electrolytic-action development between the coatings of dissimilar metals A, B.

In the embodiment of FIG. 12, an annular open ring 120, as of molded plastic material, is also the means of providing the desired electrolytic environment within an eye. As in FIG. 11, the ring 120 may be coated with the respective dissimilar metals A, B on its opposite sides. But the ring 120 of FIG. 12 has no haptics. On the other hand, interengaging formations on ring 120 and on a suitable intraocular lens 121 enable "piggy-back" assembly of ring 120 to lens 121. Specifically, in FIG. 12 these formations are in the form of angularly spaced lugs 122 having frictional or snap-action engagement with spaced peripheral locales of the intraocular lens 121.

In much of the foregoing discussion, the symbols A and B have designated the dissimilar metals of one aspect of the invention. But this will be understood to be merely for verbal simplification, in that a variety of salt compounds of the dissimilar metals, or dissimilar salts of a given metal may be utilized for generally similar electrolytic action. In the case of salts, longevity of the coating cannot match the longevity of a metal coating, in that salts will more readily disappear in solution in the course of time. But then, it must be realized that for a given therapeutic objective to be achieved, such as epithelial-cell and/or protein growth to be impeded, the greatest gain is achieved initially, i.e., immediately after surgery and capsule scraping, namely, at a time when a few epithelial cells may still remain as seedlings for epithelial-cell growth. This being the case, references herein to dissimilar metals or to dissimilar metal coatings are to be understood to apply also to dissimilar salts, i.e., to salts which exhibit sufficiently different potentials in the electrochemical series. And the same point is to be understood for the case of a metal coating at A and a salt compound at B, as long as the desired potential difference exists between coatings of dissimilar materials in the electrochemical series. Basic salts may suitably be selected from the group comprising magnesium fluoride and zinc sulfide; and any coating may include a polarizing component.

It should be further realized that for some purposes, the desired impeding of epithelial-cell and protein-strand growth can be achieved by a single coating which, in the saline-liquid environment within the eye, will provide a sufficient source of ions or electrons. Such a result can be achieved by a single coating which includes a mildly radioactive ingredient, or by a single coating of an impure metal, where the impurity is carbon or germanium, or by a single salt-containing coating.

The described invention will be seen to achieve all stated objects, and with important features and improvements, including but not limited to:

1. A method and apparatus whereby the biological balance of lens epitheliun cells can be disrupted to stop or inhibit their growth.

2. The use of optical coatings on an intraocular lens, e.g., to reduce glare.

3. The use of optical coatings on an intraocular lens to change optical transmission, e.g., to screen out ultraviolet radiation.

4. The use of lens coatings, in order to change the surface energy, and thereby change the wetting angle. Reduction in wetting angle limits the amount of deposits adhering to an intraocular lens.

5. The use of an induced electrolytic process to aid in the treatment of an eye disease, such as uveitis.

6. The use of known lens-coating technologies to accomplish one or more biological modifications.

7. The use of coating processes that are mass-related enables a measure of control of the amount of biological reactivity.

What is claimed is:

1. An intraocular-lens element comprising a lens body of transparent material configured for a predetermined optical power in the aqueous environment of a human eye, and a quantity of each of two dissimilar metals carried at spaced locations on said body, whereby to start an electrolytic action when implanted in such an environment, said dissimilar metals being benign to body fluids and selected for a difference between their respective potentials, wherein said potential difference is in the range of 0.1 to 3.5 volts.

2. The lens element of claim 1 wherein the quantities of metal are optical coatings.

3. The lens element of claim 2, wherein said lens element has an optically used surface area, and the coating area is substantially in register with the optically used surface area of the lens body.

4. The lens element of claim 1, wherein said body has front and back surfaces and said metals are in the form of angularly spaced segments on one of said surfaces, with segments of one metal in angular interlace with segments of the other metal.

5. The lens element of claim 4, wherein said metals are also in the form of angularly spaced segments on the other of said surfaces, the segments on one surface being paired in register with the segments on the other surface.

6. The lens element of claim 5, wherein one of the segment of each registering pair is of one metal and the other segment of each pair is of the other metal.

7. The lens element of claim 1, wherein said body has front and back surfaces and said metals are in the form of angularly spaced segments, the segments of one metal being on one of said surfaces and the segments of the other metal being on the other of said surfaces.

8. The lens element of claim 1, wherein the quantities of metal are in the form of spaced patterns of optical coatings of the respective metals.

9. The lens element of claim 8, wherein the spaced patterns are radially spaced concentric annuli, the pattern of one metal being in radially staggered interlace with the pattern of the other metal.

10. The lens element of claim 8, wherein said lens element has an optical axis and the spaced patterns are sector-shaped in angularly spaced relation about the optical axis, the pattern of sector shapes for one metal being angularly staggered interlace with the pattern of sector shapes for the other metal.

11. The lens element of claim 8, wherein the spaced pattern of one metal is an array of spaced parallel areas on a first direction of orientation, and wherein the spaced pattern of the other metal is an array of spaced parallel areas on a second direction that is transverse to said first direction.

12. The lens element of claim 8, wherein the pattern of one metal is a two-dimensional array of spaced rectangular areas, and the pattern of the other metal is a similar two dimensional array, the rectangular areas of the respective arrays being in spaced two-dimensional interlace.

13. The lens element of claim 1, wherein the two dissimilar metals are united to a structure that is separate from said body, said structure and said body having interengageable means for retaining said structure in assembled relation to said body.

14. The lens element of claim 13, wherein said separate structure is a circumferentially continuous ring of insulating material with axially spaced surfaces each of which carries one to the exclusion of the other metal.

15. The lens element of claim 13, wherein said interengageable means comprises angularly spaced lugs on said structure removably engageable with spaced peripheral regions of said body.

16. The lens element of claim 1, wherein said quantities are in the form of pins of the respective metals, embedded in spaced array on said body, with exposed pin ends at a surface of said body.

17. The lens element of claim 16, wherein said pins are arrayed at angular spacings on a circular locus of pin centers, the locus being centered on the optical center of said body, with the pins of the respective metals in staggered interlace.

18. The lens element of claim 1, wherein said quantities are in the form of one pin element of one of said metals and one pin element of the other of said metals, said pin elements being embedded in said body, with an exposed end of each pin end at at least one surface of said body.

19. The lens element of claim 18, wherein each pin element is a chord-truncated half cylinder, said pin elements being consolidated into a single-pin structure with a non-conductive spacer between confronting chord truncations, at least one end of said pin elements being exposed at a single surface of said body.

20. The lens element of claim 18, wherein each pin element is a cylinder of length which is less than half the thickness of said body, said pin elements being aligned in spaced end-to-end array and so embedded in said body that one end of one pin element is exposed at one surface of said body and the opposite end of the other pin element is exposed at another surface of said body.

21. The lens element of claim 1, wherein the lens element has an optical axis and the consolidated single-pin structure is on the optical axis of said lens body.

22. The lens element of claim 20, wherein the lens element has an optical axis and the end-to-end alignment of said pin elements is on the optical axis of said lens body.

23. The lens element of claim 1, wherein said lens body includes integrally formed outwardly extending haptic structure, and wherein said dissimilar metals are carried by said haptic structure.

24. The lens element of claim 1, wherein said dissimilar metals are selected from the group consisting of gold, rhodium, silver, copper, platinum, and aluminum.

25. The lens element of claim 1, wherein said body has front and back surfaces, and wherein one of said metals is on at least a part of one of said surfaces and the other of said metals is on at least a part of the other of said surfaces.

26. The lens element of claim 1, wherein the two dissimilar metals are carried peripherally of said body.

27. The lens element of claim 26, wherein said body has front and back surfaces, and wherein one of said metals is on one of said surfaces and the other of said metals is on the other of said surfaces.

28. An intraocular-lens element comprising a body of transparent material configured for a predetermined optical power in the aqueous environment of a human eye, and a quantity of basic salt affixed to a surface portion of said body, whereby to start an electrolytic action when implanted in such an environment.

29. The lens element of claim 28, in which the basic salt is in the form of a transparent optical coating.

30. The lens element of claim 29, in which the coating includes a polarizing component.

31. The lens element of claim 29, in which the coating includes a radioactive substances.

32. The lens element of claim 29, in which the basic salt is selected from the group consisting of magnesium fluoride and zinc sulfide.

33. An intraocular-lens element, comprising a body of transparent material configured for a pre-determined optical power in the aqueous environment of a human eye, and a quantity of an impure metal affixed to a portion of said body, whereby to start an electrolytic action when implanted in such an environment.

34. The lens element of claim 33, wherein the impurity in said metal involves one or more materials selected from the group consisting of carbon and germanium.

35. An intraocular-lens element comprising a lens body of transparent material having front and back surfaces and configured for a predetermined optical power in the aqueous environment of a human eye, one of said metals being on at least a part of one of said surfaces and the other of said metals being on at least a part of the other of said surfaces, and the respective areas of said metals on said surfaces being in at least partial register.

36. An intraocular-lens element comprising a lens body of transparent material having front and back surfaces and configured for a predetermined optical power in the aqueous environment of a human eye, a circumferentially continuous ring of a first metal on one of said surfaces, and a circumferentially continuous ring of a second and dissimilar metal on the other of said surfaces, whereby to start an electrolytic action when implanted in such an environment.

37. The lens element of claim 36, in which that one of said metals which has a greater potential in the electrochemical series than that of the other of said metals is on the back surface of said lens body.

38. An intraocular-lens element comprising a lens body of transparent material configured for a predetermined optical power in the aqueous environment within a human eye, and means carried by said body for promoting an electrolytic action within the eye upon implantation and exposure of said body to said environment, said means comprising at spaced locations on said body one metal and a basic salt of a metal that is dissimilar from said one metal.

39. An intraocular-lens element comprising a lens body of transparent material configured for a predetermined optical power in the aqueous environment within a human eye, and means carried by said body for promoting an electrolytic action within the eye upon implantation and exposure of said body to said environment, said means comprising at spaced locations on said body two basic salts of dissimilar metals carried at spaced locations on said body.

40. An intraocular-lens element comprising a lens body of transparent material configured for a predetermined optical power in the aqueous environment within a human eye, and means carried by said body for promoting an electrolytic action within the eye upon implantation and exposure of said body to said environment, said means comprising at spaced locations dissimilar salts of the same metal.

* * * * *